(12) United States Patent
Saunois et al.

(10) Patent No.: US 12,109,245 B2
(45) Date of Patent: Oct. 8, 2024

(54) EXTRACT OF AERIAL PARTS OF MACA RICH IN POLYPHENOLS AND COMPOSITION COMPRISING SAME

(71) Applicant: LABORATOIRES EXPANSCIENCE, Paris la Defense (FR)

(72) Inventors: Alex Saunois, Dreux (FR); Caroline Baudouin, Rambouillet (FR); Sophie Leclere-Bienfait, Dreux (FR); Sebastien Garnier, Le Rouret (FR); Philippe Msika, Versailles (FR)

(73) Assignee: Laboratoires Expanscience, Paris la Defense (FR)

( * ) Notice: Subject to any disclaimer, the term of this patent is extended or adjusted under 35 U.S.C. 154(b) by 380 days.

(21) Appl. No.: 16/580,826

(22) Filed: Sep. 24, 2019

(65) Prior Publication Data
US 2020/0085897 A1 Mar. 19, 2020

Related U.S. Application Data

(63) Continuation of application No. 13/821,668, filed as application No. PCT/EP2011/073834 on Dec. 22, 2011, now abandoned.

(30) Foreign Application Priority Data

Dec. 22, 2010 (FR) ...................................... 1061047

(51) Int. Cl.
| | |
|---|---|
| A61K 8/49 | (2006.01) |
| A23L 33/105 | (2016.01) |
| A61K 8/368 | (2006.01) |
| A61K 8/9789 | (2017.01) |
| A61K 31/05 | (2006.01) |
| A61K 31/197 | (2006.01) |
| A61K 31/198 | (2006.01) |
| A61K 31/201 | (2006.01) |
| A61K 31/341 | (2006.01) |
| A61K 31/42 | (2006.01) |
| A61K 31/57 | (2006.01) |
| A61K 31/585 | (2006.01) |
| A61K 31/715 | (2006.01) |
| A61K 31/717 | (2006.01) |
| A61K 33/30 | (2006.01) |
| A61K 36/28 | (2006.01) |
| A61K 36/31 | (2006.01) |
| A61K 36/48 | (2006.01) |

(Continued)

(52) U.S. Cl.
CPC ............ *A61K 36/31* (2013.01); *A23L 33/105* (2016.08); *A61K 8/368* (2013.01); *A61K 8/498* (2013.01); *A61K 8/9789* (2017.08); *A61K 31/05* (2013.01); *A61K 31/197* (2013.01); *A61K 31/198* (2013.01); *A61K 31/201* (2013.01); *A61K 31/341* (2013.01); *A61K 31/42* (2013.01); *A61K 31/57* (2013.01); *A61K 31/585* (2013.01); *A61K 31/715* (2013.01); *A61K 31/717* (2013.01); *A61K 33/30* (2013.01); *A61K 36/28* (2013.01); *A61K 36/48* (2013.01); *A61K 36/54* (2013.01); *A61K 36/899* (2013.01); *A61K 38/00* (2013.01); *A61K 45/00* (2013.01); *A61Q 19/08* (2013.01); *A61K 2800/805* (2013.01)

(58) Field of Classification Search
CPC ....... A61K 36/31; A61K 33/105; A61K 31/05
See application file for complete search history.

(56) References Cited

U.S. PATENT DOCUMENTS

| | | | |
|---|---|---|---|
| 2007/0280975 A1 | 12/2007 | Kato et al. | |
| 2008/0020067 A1* | 1/2008 | Koda ..................... | C12G 3/055 424/725 |

(Continued)

FOREIGN PATENT DOCUMENTS

| | | |
|---|---|---|
| CA | 2553987 A1 | 8/2005 |
| DE | 102008021586 A1 | 11/2009 |

(Continued)

OTHER PUBLICATIONS

NIH: National Institute of Diabetes and Digestive and Kidney Diseases. "Treatment for Overweight & Obesity". Reviewed on: Feb. 2018 [retrieved on: Mar. 26, 2022]. Retrieved from: <URL: https://www.niddk.nih.gov/health-information/weight-management/adult-overweight-obesity/treatment>, 5 pages. (Year: 2018).*

(Continued)

*Primary Examiner* — Aaron J Kosar
(74) *Attorney, Agent, or Firm* — Rouget F. Henschel; Potomac Law Group, PLLC

(57) ABSTRACT

The invention relates to an extract of aerial parts of Maca rich in polyphenols, and also to a composition comprising such an extract and, where appropriate, a suitable excipient. The invention also relates to a process for extracting an extract of aerial parts of Maca rich in polyphenols, and also to the extract that can be obtained by means of said process. The invention also relates to such a composition or such an extract for use thereof in preventing or treating disorders or pathological conditions of the skin, the mucous membranes or the superficial body growths and/or for use thereof in preventing and/or treating vascular disorders. Finally, the invention relates to a cosmetic care process for the skin, the superficial body growths or the mucous membranes, with a view to improving the condition thereof or the appearance thereof, which comprises the administration of such a composition or of such an extract.

14 Claims, 1 Drawing Sheet

(51) Int. Cl.
*A61K 36/54* (2006.01)
*A61K 36/899* (2006.01)
*A61K 38/00* (2006.01)
*A61K 45/00* (2006.01)
*A61Q 19/08* (2006.01)

(56) References Cited

U.S. PATENT DOCUMENTS

| 2008/0206431 | A1 | 8/2008 | Matsumoto et al. | |
| 2008/0260874 | A1* | 10/2008 | Koda | A61P 9/00 424/755 |
| 2009/0269424 | A1* | 10/2009 | Koda | A23L 33/105 424/725 |

FOREIGN PATENT DOCUMENTS

| EP | 1714635 | A1 | | 10/2006 | | |
| EP | 1743934 | B1 | | 10/2010 | | |
| FR | 2885052 | A1 | | 11/2006 | | |
| JP | 2001039854 | A | | 2/2001 | | |
| JP | 2005281271 | A | * | 10/2005 | ............... | A23C 9/13 |
| JP | 2005281272 | A | * | 10/2005 | ............... | A23G 3/36 |
| JP | 2007031371 | A | | 2/2007 | | |
| JP | 2007230987 | A | | 9/2007 | | |
| JP | 2009067763 | A | | 4/2009 | | |
| JP | 2010235533 | A | | 10/2010 | | |

OTHER PUBLICATIONS

Mayo Clinic. "Wrinkles". Retrieved from the internet on: Mar. 26, 2022. Retrieved from: <URL: https://my.clevelandclinic.org/health/diseases/21882-poor-circulation>, 4 pages. (Year: 2022).*
Cleveland Clinic. "Poor Circulation". Reviewed on: Sep. 27, 2021 [retrieved from the internet on: Mar. 26, 2022]. Retrieved from: <URL: https://www.mayoclinic.org/diseases-conditions/wrinkles/diagnosis-treatment/drc-20354931?p=1>, 12 pages. (Year: 2021).*
JP 2005281271 A—Derwent machine transition, 11 pages (Year: 2005).*
Connect Chemicals; bio-Propanediol data sheet, 2017.
Kalathenos et al., "Ethanol as a food preservative", 2003, in Russel N.J., Gould G.W. (eds) Food Preservatives, Springer, Boston, MA.
Li et al., "Glucosinolate Contents in Maca (*Lepidium peruvianum* Chacon) Seeds, Sprouts, Mature Plants and Several Derived Commercial Products," Economic Botany, vol. 55, No. 2, pp. 255-262, 2001.
Perrigo Australia; Material Safety Data Sheet: Glycerol B.P.; GL Y00790F_MSDS.doc_Jun. 7, 2013.
Tellez et al., "Composition of the essential oil of *Lepidium meyenii* (Walp)", Phytochemistry, Pergamon Press, GB, vol. 61, No. 2, Sep. 2002, pp. 149-155.
ZEMEA Propanediol for Skin Care brochure; DuPont Tate & Lyle BioProducts, 2017.

* cited by examiner

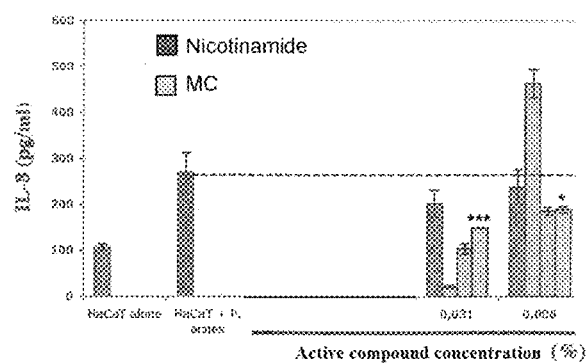

EXTRACT OF AERIAL PARTS OF MACA RICH IN POLYPHENOLS AND COMPOSITION COMPRISING SAME

The invention relates to an extract of aerial parts of Maca (*Lepidium meyenii*), advantageously an extract of Maca leaves, rich in polyphenols, and more particularly rich in flavonoids, and a composition comprising such an extract. The composition is advantageously cosmetic, pharmaceutical, dermatological or nutraceutical.

The invention also relates to a process for extracting an extract of aerial parts of Maca rich in polyphenols and more particularly flavonoids, and the extract suitable for being obtained by said process.

The invention also relates to such a composition or such an extract for the use thereof for preventing or treating disorders or pathologies of the skin, the mucous membranes or superficial body growths, for the use thereof for preventing or treating vascular disorders, inflammatory reactions or pathologies, or for the use thereof for preventing or treating adipose tissue regulations or for preventing or treating dermal tissue alterations. Finally, the invention relates to a cosmetic care process for the skin, superficial body growths or mucous membranes, with a view to improving the condition thereof or the appearance thereof, comprising the administration of such a composition or of such an extract.

The Maca Plant (*Lepidium meyenii*)
Botanical and Agronomic Aspects

Maca, *Lepidium meyenii* Walp, is a member of the Brassicaceae (Cruciferae) family and is a small herbaceous plant of 12 to 20 cm in height. The underground part thereof measures 2 to 5 cm. It comprises a taproot topped with the lower part of an enlarged fleshy hypocotyl. When dry, the whole resembles the shape of a small turnip. Depending on the cultivars, the hypocotyls display a wide array of colours from purple to light yellow.

The pinnatifid leaves form a rosette and are renewed from the centre thereof. The small flowers are self-pollinating. The fruit is a small siliqua (4 to 5 mm) with two valves each comprising a seed.

Chemical Compounds of the Seed and Aerial Parts

The literature does not report any chemical data in relation to these parts of the Maca plant. It should be noted that the seeds of several *Lepidium* species grown in the United States contain significant quantities of fat (16 to 31%).

Biological Properties

Studies published on the pharmacological properties of Maca are very rare.

The reputation of the effect of the Maca tuber on fertility was confirmed by a pharmacological study conducted on rats. This study revealed an increase in fertility probably due to increased Graafian follicle development. The general articles reporting this information refer to data which are difficult to access including one Peruvian thesis submitted in 1961.

Uses

The Maca tuber or Maca hypocotyls or roots growing underground have already been used in the prior art.

In particular, the nutritional value of the Maca tuber, similar to cereals conventionally used in food, makes it a food of choice of major interest for the populations of Peruvian plateaux. It is consumed fresh (in the form of a fermented beverage, cooked under ash), cooked (in jam or cake form) or dried (mixed and boiled with water or milk in porridge or purée form).

The Maca tuber has been in popular use for hundreds of years for medicinal purposes to increase the fertility of animals and humans. In this way, Spanish conquistadors are said to have increased the low reproduction of their livestock using Maca.

The Kallawaya, itinerant Andean healers, prescribed a decoction of thinly sliced fresh tuber for sterile women seeking to be fecundated, three or four days after their last menstrual period.

The tuber is also used fresh, boiled and reduced to purée in an abdominal poultice to induce menstruation.

At the present time, Maca is increasing in popularity due to the stimulant and aphrodisiac properties attributed thereto. The Maca tuber is associated (improperly due to a promising potential market) with ginseng (*Panax ginseng*), hence the name Peruvian *ginseng*. The aphrodisiac power of the tuber would appear to be due to the presence of prostaglandins and sterols.

Further uses of the tuber include the benefit thereof in case of respiratory disorders (tuberculosis), chronic fatigue, memory disorders, menopausal symptoms, as a therapy for rheumatism attacks, or for the laxative effect thereof. However, none of these indications has been objectivized by scientific research.

Moreover, the aerial parts of Maca are generally considered to be waste, and thus have never been used or upgraded for cosmetic, dermatological, pharmaceutical or nutraceutical purposes.

BRIEF DESCRIPTION OF THE DRAWING

FIG. 1 is a graph showing production of IL8 by keratinocytes stimulated with *P. acnes* as a function of the active substance concentration in %.

DESCRIPTION OF THE INVENTION

The inventors discovered that extracts of aerial parts of Maca (*Lepidium meyenii*), particularly the extract of leaves, stems, flowers, or seeds, and advantageously the extracts of leaves, have cosmetic, dermatological or pharmaceutical properties never previously described to date.

In particular, it is the first time that extracts of aerial parts of Maca have been used as such, for the specific properties thereof, particularly with a view to enhancing skin firmness or tonicity, or as anti-ageing agents.

The invention relates to an extract of aerial parts of Maca rich in polyphenols, typically containing at least 1% by weight of polyphenols, expressed in gallic acid equivalents, with respect to the weight of the dry extract.

Advantageously, the extract of aerial parts of Maca contains at least 3%, advantageously at least 5%, by weight of polyphenols, expressed in gallic acid equivalents, with respect to the total weight of the dry extract.

The term extract of aerial parts of Maca rich in polyphenols refers to an extract obtained by means of processes for concentrating the polyphenols potentially present in the aerial parts of Maca such that the extract contains at least 1% by weight of polyphenols, preferably at least 3% by weight and more advantageously at least 5% by weight expressed in gallic acid equivalents with respect to the total weight of the dry extract, typically using the Folin-Ciocalteu assay method.

According to one advantageous alternative embodiment of the invention, the extract contains, expressed in gallic acid equivalents with respect to the dry extract obtained, 1% to 30% by weight of polyphenols, advantageously 3% to 20% by weight of polyphenols, more advantageously 5% to 10% by weight of polyphenols.

The dry extract content in the extract according to the invention varies from 0.01 to 90%, advantageously from 0.5 to 50%, more advantageously from 0.5 to 15%, even more advantageously from 0.5 to 5%, by weight with respect to the total weight of the extract.

Particularly advantageously according to the invention, the polyphenols are flavonoids, such as flavonols.

According to one particular feature of the present invention, the extract according to the present invention contains at least 0.2%, advantageously at least 0.5%, by weight of flavonoids, expressed in rutin equivalents, with respect to the total weight of the dry extract, typically by means of the aluminium chloride assay method.

Advantageously, the extract of aerial parts of Maca contains at least 1%, advantageously at least 2%, by weight of flavonoids, in particular between 1 and 5%, very particularly between 2 and 4%, by weight, expressed in rutin equivalents, with respect to the total weight of the dry extract.

Typically, the flavonoids of the extract according to the invention are flavonols, advantageously chosen from the group consisting of quercetin, kaempferol, derivatives thereof such as glycosylated derivatives thereof, and the mixtures thereof.

In one particular embodiment of the present invention, the flavonoids contain quercetin and kaempferol, derivatives thereof such as glycosylated derivatives thereof, or mixtures thereof advantageously at a concentration of at least 30%, typically at least 50%, by weight, particularly at least 70%, advantageously at least 80%, more advantageously at least 90%, expressed in rutin equivalents, with respect to the total weight of the flavonoids.

According to one advantageous alternative embodiment of the invention, the extract further contains 0% to 70%, advantageously 10 to 60%, more advantageously 20 to 50%, more advantageously 30 to 40%, by weight of sugars, the % being expressed by weight with respect to the total weight of the dry extract, typically by means of the HPLC assay method.

Moreover, the extract according to the invention advantageously contains 0 to 50% by weight, more advantageously 0 to 20% by weight, even more advantageously 0 to 10% by weight of fat, the % being expressed by weight with respect to the total weight of the dry extract.

Moreover, the extract according to the invention advantageously contains 0 to 60% by weight, more advantageously 0.5 to 30% by weight, even more advantageously 0.5 to 10%, by weight of protein, the % being expressed by weight with respect to the total weight of the dry extract, typically by means of the Bradford assay method.

Within the scope of the present invention, the aerial parts of Maca are chosen from the group consisting of leaves, stems, flowers, seeds, or mixtures thereof.

Maca tubers, Maca hypocotyls, and Maca roots, growing underground, are thus not included in the aerial parts of Maca according to the present invention.

Particularly advantageously, the aerial parts are Maca leaves.

This extract is advantageously obtained by means of solid-liquid extraction of the fresh or dried aerial parts of Maca in a solvent chosen from the group consisting of water, alcohols such as ethanol, glycerols, glycols such as propanediol, and mixtures thereof such as binary mixtures, in proportions between 0% and 100% water with respect to the other solvents, more advantageously in proportions between 0% and 90% water with respect to the other solvents.

Mostly, binary solvent mixtures such as water and one solvent chosen from ethanol, glycerol or propanediol are used.

In one particular embodiment, the extraction solvent is a hydro-alcoholic solvent, such as a water-ethanol mixture, hydro-glycerolic and/or hydro-glycolic, such as a water-propanediol mixture, advantageously in a proportion between 30 and 90% alcohol, glycerol and/or glycol in water.

More particularly, within the scope of the solid-liquid extraction of the fresh or dried aerial parts of Maca, between 0.1 and 50% by weight (in dry matter equivalent) of desired plant parts is introduced into the extraction solvent, preferentially between 1 and 10% by weight, typically 5% by weight (the % being expressed by weight of the dry matter with respect to the total weight used). The dried part of Maca may be leaves, stems, flowers, seeds, alone or in association, and preferentially leaves.

In particular, in the presence of ethanol, a proportion between 0 and 100% ethanol in water, preferentially between 10 and 80% ethanol, and advantageously between 70 and 90% is chosen (the % are expressed by weight of ethanol with respect to the total weight of water+ethanol).

In particular, in the presence of glycerol, a proportion between 0 and 100% glycerol in water, preferentially between 30 and 80%, and advantageously 50% (the % are expressed by weight of glycerol with respect to the total weight of water+glycerol).

In particular, in the presence of glycol and more particularly propanediol, a proportion between 0 and 100% of propanediol in water, preferentially between 10 and 80%, and advantageously 80%, is chosen (the % are expressed by weight of propanediol with respect to the total weight of water+propanediol).

The extraction temperature is advantageously between 4° C. and 100° C., and preferentially between 10° C. and 60° C., and more particularly between 15° C. and 30° C.

The extraction time varies advantageously from 30 minutes to 4 hours, and preferentially from 30 minutes to 2 hours, and more advantageously is approximately 1 hour.

Following extraction, the residual dry matter is advantageously separated from the liquid phase, for example by filtration, settling or centrifugation. The liquid phase obtained may be filtered using filters of suitable porosity so as to obtain a clear solution.

These first separation steps may be followed by purification steps, for example by ultrafiltration and/or nanofiltration, for concentrating the molecules of potential interest to the detriment of others.

The extract obtained may be in liquid form but may also be dried using methods known to those skilled in the art, such as spray-drying or freeze-drying with or without a substrate such as maltodextrin.

The invention also relates to a process for preparing an extract of aerial parts of Maca, advantageously Maca leaves, comprising at least one step for solid-liquid extraction of the aerial parts of Maca in a solvent chosen from the group consisting of water, alcohols such as ethanol, glycerols, glycols such as propanediol, and mixtures thereof.

Typically, the process comprises the following successive steps:
  (a) dispersion and extraction in a suitable solvent of aerial parts of Maca and advantageously leaves, the solvent being advantageously an aqueous and/or alcoholic and/or glycerolic and/or glycolic solvent,
  (b) centrifugation and/or filtration of the extract obtained following step (a);

(c) if applicable, ultrafiltration and/or diafiltration and/or nanofiltration of the extract obtained following step (b); and (d) recovery of the extract of aerial parts of Maca; and (e) optional drying of the extract obtained in step (d) optionally on a substrate.

During step (a), the aerial parts, particularly the leaves, are advantageously used in the following proportions: between 0.1 and 50% of dry matter of leaves, and preferentially between 5 and 20%, and typically 5%, the percentages being expressed by weight of the dry matter with respect to the total weight used (aerial parts+solvent).

The extraction in step (a) is advantageously performed under stirring. No enzyme is added.

During step (a), the following solvents are advantageously used alone or mixed with water:ethanol, glycerol or propanediol, in a proportion advantageously between 30 and 90% of these solvents in water and more advantageously between 50 and 80% (the % are expressed by weight of solvent with respect to the total weight of solvent+water).

The invention also relates to a composition comprising as the active compound an extract of aerial parts of Maca, optionally in association with a suitable excipient.

The composition is advantageously cosmetic, pharmaceutical, dermatological or nutraceutical.

Said composition is preferably formulated for external topical or oral administration.

According to one advantageous alternative embodiment of the invention, the composition contains 0.001 to 10%, typically 0.01 to 5%, advantageously between 1 and 5%, by weight of extract, expressed as a percentage of dry extract.

According to a further aspect of the invention, the composition further comprises at least one further active compound in addition to the extract of aerial parts of Maca.

This further compound may be chosen from all the compounds and the functional equivalents thereof, listed hereinafter.

This further compound may particularly be chosen from the active compounds conventionally used in dermatology, pharmaceuticals or cosmetics and known to those skilled in the art, such as emollients, moisturising agents, keratoregulators, keratolytics, skin barrier healing and/or remodelling agents, PPAR, RXR or LXR agonists, sebo-regulating agents, anti-irritant and/or anti-inflammatory and/or soothing agents, anti-oxidant agents, anti-ageing agents, depigmenting or hypopigmenting agents, pigmenting agents, lipolytic agents or lipogenesis inhibitors or anti-cellulite or slimming agents, mineral or organic sun filters and screens (pigment or ultra-fine), antifungal compounds, preservatives, antibacterial agents, pre and probiotics, antibiotics, immunomodulators.

More particularly, the skin barrier healing and/or remodelling agents suitable for use in association are advantageously panthenol (vitamin B5), arabinogalactan, zinc oxide, ceramides, cholesterol, squalane and phospholipids.

The sebo-regulating agents suitable for use in association are advantageously chosen from the group consisting of 5-alpha reductase inhibitors. Zinc (and zinc derivatives such as the gluconate, salicylate and pyroglutamic acid salts thereof) and spironolactone, also have a sebo-suppressive activity. Further sebo-regulating agents of lipid origin acting on sebum quality, such as linoleic acid, are of interest.

The anti-inflammatory and/or anti-irritant and/or soothing agent may be arabinogalactan.

The hypopigmenting or depigmenting agents particularly include N-undecylenoyl-L-phenylalanine (Sepiwhite®).

The sun protection active compounds suitable for use in association are advantageously UVB and/or UVA sun filters or screens; such as mineral and/or organic sun screens or filters known to those skilled in the art who will adapt the choice and concentrations thereof according to the degree of protection sought.

The preservatives suitable for use in association are for example those generally used in cosmetics and in nutraceuticals, molecules with antibacterial activity (pseudo-preservatives) such as caprylic derivatives such as for example capryloyl glycine and glyceryl caprylate; hexanediol, sodium levulinate, and zinc and copper derivatives (gluconate and PCA).

The active compounds recommended in association with the extract according to the invention include plant extracts, in particular:

Plant oils such as soybean and/or rapeseed oil, avocado oil (WO2004/012496, WO2004/012752, WO2004/016106, WO2007/057439), lupin oil, advantageously sweet white lupin oil (WO 98/47479), or a mixture of these oils;

the oleodistillate or concentrates of plant or animal oils, particularly sunflower, more advantageously linoleic sunflower concentrates, such as sunflower oil concentrated in unsaponifiables (Soline®) (see the international application WO 01/21150) marketed by Laboratoires Expanscience, oils concentrated in unsaponifiable such as avocado, rapeseed, corn or palm oil, particularly useful for the moisturising and/or emollient, skin barrier healing and/or remodelling, anti-inflammatory and/or anti-irritant and/or soothing activity thereof;

plant or plant oil unsaponifiables, advantageously avocado furans (Avocadofurane®), suitable for being obtained by means of the process described in the international application WO 01/21605, avocado and/or soybean unsaponifiables, more particularly a mixture of furan avocado unsaponifiables and soybean unsaponifiables, advantageously in a respective ratio of approximately 1:3-2:3 (such as Piascledine®), soybean unsaponifiables (as obtained according to the process described in the international application WO01/51596), sterol unsaponifiables (typically unsaponifiables wherein the sterol, methylsterol and triterpene alcohol content is between 20 and 95% by weight, preferably 45-65% by weight, with respect to the total weight of the unsaponifiable), plant sterols, sterol esters and vitamin derivatives, particularly useful for the skin barrier healing and/or remodelling, anti-ageing, anti-inflammatory activity thereof;

plant peptides or amino acid complexes, in particular avocado peptides (such as those described in the international application WO2005/105123), lupin peptides (such as those obtained according to the process described in the application WO2005/102259), quinoa peptides (such as those described in the international application WO2008/080974), Maca peptides such as those described in the international application WO2004/112742), optionally fermented soybean peptides, rice peptides (such as those described in the international application WO 2008/009709), particularly useful for the moisturising and/or emollient (avocado), kerato-regulating (lupin, quinoa), skin barrier healing and/or remodelling (maca, quinoa, soybean), anti-inflammatory and/or anti-irritant and/or soothing (lupin, quinoa), antioxidant (avocado), anti-ageing (lupin, maca), pigmenting (rice) activity thereof;

plant sugars, particularly avocado sugars (such as those described in the application WO2005/115421), particularly useful for the kerato-regulating, skin barrier healing and/or remodelling, anti-inflammatory and/or anti-irritant and/or soothing activity thereof;

butyl avocadate (5 alpha Avocuta®), a 5-alpha reductase inhibitor (see WO 01/52837 and WO 02/06205), typically regulating increased seborrhoea secretion in acne or dandruff;

extracts rich in polyphenols, and more particularly avocado fruit extracts (such as that described in the application FR 1 061 047) and an extract of aerial parts of *Gynandropsis gynandra* (FR 1061051);

lupeol (FR 2 822 821, FR 2 857 596) particularly useful for promoting healing, lupin total extract (such as those described in the international application WO2005/102259), particularly suitable for treating irritation;

Cupuaçu butter, particularly appreciated for the moisturising properties thereof;

an extract of *Acacia macrostachya* seeds (FR 0958525), *Schizandra sphenanthera* seeds (FR 0955343 and FR 0955344) and *Vigna unguiculata* seeds (FR 0958529).

The active compounds recommended in association with the extract according to the invention include oxazolines, particularly those chosen from the group consisting of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline, preferably 2-undecyl-4,4-dimethyl-1,3-oxazoline (OX-100 or Cycloceramide®; WO2004050052, WO2004050079, and WO2004112741). They are particularly useful for the anti-inflammatory and/or anti-irritant and/or soothing, antioxidant, depigmenting, immunomodulating activity thereof.

The active compounds recommended in association with the extract according to the invention include 5-alpha reductase inhibitors, such as butyl avocadate (5 Alpha Avocuta®).

All these associations comprise at least one further active compound, in addition to the extract of aerial parts of Maca, and may comprise two, three, four or more active compounds as described above.

The composition according to the invention may be formulated in the form of various preparations suitable for topical administration, oral, rectal, vaginal, nasal, auricular or bronchial administration, and for parenteral administration.

The composition according to the invention is advantageously formulated in the form of various preparations suitable for topical administration, more particularly for application on the skin and/or superficial body growths and/or mucous membranes.

According to a first alternative embodiment, the various preparations are suitable for topical administration and particularly include creams, emulsions, milks, ointments, lotions, oils, aqueous or hydro-alcoholic or glycolic solutions, powders, patches, sprays, shampoos, varnishes or any other product for external application.

According to a second alternative embodiment, the various preparations are suitable for oral administration; the extract of aerial parts of Maca being suitable for use either in a dietary supplement or in a nutraceutical composition. The dietary supplement may be in the form of the extract of aerial parts of Maca per se or in the form of hard or soft gelatin or plant capsules within the scope of the present invention. In this case, said dietary supplement may contain 10 to 100% by weight of aerial parts of Maca.

The optimal modes of administration, dosages and pharmaceutical forms of the compounds and compositions according to the invention may be determined according to criteria generally taken into account for determining a pharmaceutical, particularly dermatological, cosmetic or veterinary treatment suitable for a patient or an animal, such as for example the age or body weight of the patient or animal, the severity of the state of health, tolerance of the treatment, side effects observed, skin type. According to the type of administration sought, the composition and/or the active compounds according to the invention may further comprise at least one pharmaceutically acceptable, particularly dermatologically acceptable, excipient, or a cosmetically acceptable excipient. According to the first alternative embodiment, an excipient suitable for external topical administration is used. The composition according to the present invention may further comprise at least one pharmaceutical or cosmetic adjuvant known to those skilled in the art, chosen from thickening agents, preservatives, fragrances, colorants, chemical or mineral filters, moisturising agents, spring waters, etc.

The composition comprising an extract of aerial parts of Maca having the specifications described is particularly intended for cosmetic, pharmaceutical, dermatological or nutraceutical use.

Within the scope of cosmetic, pharmaceutical or dermatological use, the composition will be advantageously formulated in the form of a preparation suitable for topical administration.

Within the scope of use for nutraceutical or cosmetic purposes ("cosmet-food"), the composition will be advantageously formulated in the form of a preparation suitable for oral administration.

The invention also relates to the use of an extract of aerial parts of Maca for manufacturing a cosmetic, pharmaceutical, dermatological composition or a nutraceutical composition.

Advantageously, the composition or extract according to the present invention is used for preventing and/or treating disorders or pathologies of the skin and/or mucous membranes and/or superficial body growths.

Particularly advantageously, the extract or composition according to the invention is used in cosmetic applications, advantageously by the topical route, particularly for care or hygiene of the skin and/or mucous membranes and/or superficial body growths such as hair, or for preventing and/or treating disorders of the skin and/or mucous membranes and/or superficial body growths such as hair.

The composition or extract according to the present invention may also be advantageously used for preventing and/or treating vascular disorders.

The composition or extract according to the invention is particularly useful for strengthening blood vessels, vessel walls and tonicity and/or for acting on blood circulation stimulation, and/or for acting on endothelial cells and thus contributing to a draining effect to combat heavy legs, rings under eyes, cellulite, skin slackening.

Strengthening vessel tonicity promotes vasoconstriction and maintenance of vessel wall homeostasis.

The composition or extract according to the present invention may also be advantageously used for preventing and/or treating dermal tissue alterations.

Examples of dermal tissue alterations include dermal matrix imbalances such as wrinkles, healing problems, skin firmness or elasticity.

In this way, the composition or extract according to the invention is also advantageously used for preventing ageing, particularly intrinsic ageing or photo-induced ageing and stretch-marked skin.

The composition or extract according to the present invention may also be advantageously used for preventing and/or treating adipose tissue regulations, and more particularly for combating the accumulation of adipose tissue and skin with cellulite.

In particular, the composition or extract according to the invention is intended for preventing and/or treating allergic, inflammatory, irritant reactions or pathologies, barrier or homeostasis disorders of immature, normal or mature/aged skin, superficial body growths (hair and nails) and/or mucous membranes (gums, periodontium, genital mucosa).

The term barrier disorders of the skin, superficial body growths and/or mucous membranes refers to disorders involving the external layer of the epidermis.

The term homeostasis disorders of the skin, superficial body growths and/or mucous membranes refers to disorders resulting from cell renewal and equilibrium processes such as psoriasis, nappy rash, atopic dermatitis, dry skin (xerosis), dehydrated skin and photosensitive skin.

Advantageously, the composition or extract according to the invention may be used for preventing and/or treating reactions, disorders or pathologies:
- of the skin, such as acne, rosacea or blotching, psoriasis, nappy rash, atopic dermatitis, eczema, contact dermatitis, irritant dermatitis, allergic dermatitis, seborrhoeic dermatitis (cradle cap), sensitive skin, reactive skin, dry skin (xerosis), dehydrated skin, skin with flushing, cutaneous erythema, photosensitised skin, pigmented skin (melasma, post-inflammatory pigmentation, etc.), depigmented skin (vitiligo), sores, chaps, stings, cracked skin particularly on breasts, sunburn, inflammations due to radiations of all kinds, irritations by chemical, physical (for example stretching for pregnant women), bacteriological, fungal or viral, parasitic (lice, scabies, tinea, dust mites, dermatophytes), radiological agents or due to natural (antimicrobial peptides) or acquired (cellular, humoral, cytokines) immune deficiency, and/or
- of the mucous membranes such as the gums and periodontia liable to present with gingivitis (sensitive gums in newborns, hygiene problems, due to smoking or other reasons), periodontopathic conditions, or of the genital mucosa liable to present with irritation of the external or internal male or female genital tracts and/or
- of superficial body growths such as nails (brittle, weak nails, etc.) and hair (alopecia, dandruff, hirsutism, seborrhoeic dermatitis, folluciliitis), whether immature, normal or mature, particularly presenting with scalp disorders such as androgenetic, acute, localised, cicatricial, congenital, newborn occipital, or areata alopecia (or baldness), due to chemotherapy/radiotherapy or telogen effluvium, anagen effluvium, hair dystrophy, trichotillomania, tinea or greasy or dry dandruff.

The invention also relates to a cosmetic care process for the skin, superficial body growths or mucous membranes, with a view to improving the condition thereof and/or the appearance thereof, comprising the administration of a cosmetic composition or an extract according to the present invention.

In one embodiment of the cosmetic process according to the invention, the composition or extract according to the invention is used for enhancing the firmness, elasticity or tonicity of the skin, or for preventing the lack of firmness or tonicity or elasticity of the skin, or for synthetizing and/or protecting the extracellular matrix, or for preventing and/or treating dermal tissue alterations.

In a further embodiment of the cosmetic process according to the invention, the composition or extract according to the invention is used as an anti-ageing agent for the skin, superficial body growths or mucous membranes, particularly against intrinsic or extrinsic ageing, namely as an anti-photo-ageing agent or anti-UV agent, or as an agent for combating the accumulation of adipose tissue and skin with cellulite.

In a further embodiment of the cosmetic process according to the invention, the skin and/or superficial body growths and/or mucous membranes in question are advantageously those with a circulation or vessel tonicity disorder.

Example 1

Dried and ground Maca leafy stems are suspended under stirring at 5% in a 10/90 w/w ethanol/water mixture for 1 hour at ambient temperature. The residual dry matter is separated from the liquid phase either by filtration, settling or centrifugation and the liquid phase obtained may be filtered using filters of suitable porosity so as to obtain a clear solution. The extract obtained has the following features:

Dry extract: 1.8%
Total sugars (HPLC): 32%/dry
Total polyphenols (Folin-Ciocalteu): 5.7%/dry
Total flavonoids (AlCl3): 1.7%

This extract has an "in tube" anti-radical, anti-DPPH activity, for which the half maximal inhibitory concentration (IC50) was determined and is 0.29 mg of dry extract, representing 20 µg of polyphenols in the reaction medium.

Example 2

Dried and ground Maca leafy stems are suspended under stirring at 5% in a 50/50 w/w glycerol/water mixture for 1 hour at ambient temperature. The residual dry matter is separated from the liquid phase either by filtration, settling or centrifugation and the liquid phase obtained may be filtered using filters of suitable porosity so as to obtain a clear solution. The extract obtained has the following features:

Dry extract: 1.8%
Total sugars (HPLC): 37%/dry
Total polyphenols (Folin-Ciocalteu): 6.4%/dry
Total flavonoids (AlCl3): 2.2%/dry This extract has an "in tube" anti-radical, anti-DPPH activity, for which the half maximal inhibitory concentration (IC50) was determined and is 0.26 mg of dry extract, representing 16.5 µg of polyphenols in the reaction medium.

Example 3

Dried and ground Maca leafy stems are suspended under stirring at 5% in an 80/20 w/w propanediol/water mixture for 1 hour at ambient temperature. The residual dry matter is separated from the liquid phase either by filtration, settling or centrifugation and the liquid phase obtained may be filtered using filters of suitable porosity so as to obtain a clear solution. The extract obtained has the following features:

Dry extract: 1.1%
Total sugars (HPLC): 40%/dry
Total polyphenols (Folin-Ciocalteu): 7.6%/dry
Total flavonoids (AlCl3): 3.6%

This extract has an "in tube" anti-radical, anti-DPPH activity, for which the half maximalinhibitory concentration (IC50) was determined and is 0.28 mg of dry extract, representing 22.5 μg of polyphenols in the reaction medium.

Example 4: Composition for Topical Application

The inventors describe hereinafter a plurality of compositions for topical application. The extracts of aerial parts of Maca (Maca AP) may be incorporated in various cosmetic products, such as cleansing solutions, oil in water emulsions, water in oil emulsions, oils, milks, lotions, shampoos, foaming products and sprays, the compositions whereof are described below. The percentages represent the weight of the product with respect to the total weight of the composition.

Cleansing Water for Sensitive Skin

| Trade or INCI name | % |
|---|---|
| CAPRYLOYL GLYCINE | 0 to 1% |
| SODIUM HYDROXIDE | 0 to 1% |
| SEQUESTRANT | 0 to 1% |
| BUTYLENE GLYCOL | 1 to 5% |
| BETA CAROTENE | 0 to 2% |
| Maca leaf extract | 0.01 to 10% |
| PRESERVATIVES | 0 to 1% |
| PEG-32 | 1 to 5% |
| PEG-7 PALMCOCOATE | 1 to 5% |
| ZINC GLUCONATE | 0 to 1% |
| CITRIC ACID | 0 to 1% |
| PURIFIED WATER | q.s. 100% |
| PARFUM | 0 to 1% |
| POLOXAMER 184 | 1 to 5% |

Anti-Ageing Emulsion

| Trade or INCI name | % |
|---|---|
| LIQUID ISOPARAFFIN | 5 to 20% |
| ISOCETYL STEARATE | 5 to 20% |
| AL—MG HYDROXYSTEARATE | 5 to 20% |
| ABIL WE 09 | 1 to 5% |
| GLYCEROL | 1 to 5% |
| VASELINE OIL | 1 to 5% |
| MICRONISED ZINC OXIDE | 1 to 5% |
| BUTYLENE GLYCOL | 1 to 5% |
| RETINOL | 0 to 1% |
| VITAMIN C | 0 to 5% |
| Maca leaf extract | 0.01 to 10% |
| ISONONYL ISONONANOATE | 1 to 5% |
| BEESWAX | 1 to 5% |
| SODIUM TARTRATE | 1 to 5% |
| SODIUM CHLORIDE | 0 to 5% |
| GLYCINE | 1 to 5% |
| PRESERVATIVES | 0 to 1% |
| CHOLESTEROL | 0 to 1% |
| PHYTOSPHINGOSINE | 0 to 1% |
| TARTARIC ACID | 0 to 1% |
| PURIFIED WATER | q.s. 100% |

Remodelling Emulsion

| Starting material/Trade or INCI name | % |
|---|---|
| HYDROGENATED POLYDECENE | 5 to 20% |
| LAURYLGLUCOSIDE-GLYSTEARATE | 1 to 5% |
| DICAPRYLYL CARBONATE | 1 to 5% |
| GLYCEROL | 5 to 20% |
| CARBOPOL | 0 to 1% |
| XANTHAN GUM | 0 to 1% |
| ASIATIC ACID | 0 to 1% |
| VITAMIN B5 | 0 to 5% |
| Maca leaf extract | 0.01 to 10% |
| SODIUM HYDROXIDE | 0 to 1% |
| PRESERVATIVES | 0 to 1% |
| CITRIC ACID | 0 to 1% |
| PURIFIED WATER | q.s. 100% |

Milk for Dry, Atopic Skin

| Starting material/Trade or INCI name | % |
|---|---|
| SWEET ALMOND OIL | 1 to 5% |
| CORN OIL | 1 to 5% |
| STEARIC ACID | 1 to 5% |
| C16 C18 CETYL ALCOHOL | 0 to 1% |
| ANTIFOAM 70414 | 0 to 1% |
| LAURIC ACID 11OE | 1 to 5% |
| PEG 300 MONOLAURATE | 0 to 1% |
| GLYCEROL MONOLEATE | 0 to 1% |
| GLYCEROL MONOSTEARATE | 1 to 5% |
| VITAMIN B12 | 0 to 5% |
| Maca leaf extract | 0.1 to 10% |
| PRESERVATIVES | 0 to 1% |
| CITRIC ACID | 0 to 1% |
| TRISODIUM CITRATE | 0 to 1% |
| PURIFIED WATER | q.s. 100% |
| PARFUM | 0 to 1% |
| GROUNDNUT OIL | 1 to 5% |
| HYDROGENATED PALM KERNEL OIL | 1 to 5% |

Soothing Spray

| Starting material/Trade or INCI name | % |
|---|---|
| PURIFIED WATER | q.s. 100% |
| TRILAURETH-4 PHOSPHATE | 1 to 5% |
| DICAPRYLYL CARBONATE | 1 to 5% |
| BUTYLENE GLYCOL | 1 to 5% |
| ERYTHRITYL ESTER | 1 to 5% |
| FLUID VASELINE OIL | 1 to 5% |
| SHEA BUTTER | 0 to 1% |
| VEGETABLE OIL | 0 to 1% |
| PRESERVATIVES | 0 to 1% |
| LYCOPENE | 0 to 5% |
| Maca leaf extract | 0.01 to 10% |
| SODIUM HYDROXIDE | 0 to 1% |
| PARFUM | 0 to 1% |
| XANTHAN GUM | 0 to 1% |
| CARBOPOL | 0 to 1% |
| SEQUESTRANT | 0 to 1% |
| CITRIC ACID | 0 to 1% |

Anti-Dandruff Shampoo

| Starting material/Trade or INCI name | % |
|---|---|
| PURIFIED WATER | q.s. 100% |
| LAUROAMPHOACETATE | 5 to 20% |
| COCOGLUCOSIDE | 5 to 20% |
| PEG 6000 DISTEARATE | 1 to 5% |
| PRESERVATIVES | 0 to 2% |
| VITAMIN F | 0 to 5% |
| PIROCTONE OLAMINE | 0 to 2% |
| Maca leaf extract | 0.01 to 10% |
| ZINC PYRITHIONE | 0 to 1% |
| PH ADJUSTER | 0 to 1% |
| SEQUESTRANT | 0 to 1% |
| PARFUM | 0 to 1% |

Example 5: Composition for Oral Administration

The Maca leaf extracts are incorporated into oral compositions, in compositions suitable for administering 50 mg to 200 mg of Maca leaf extract per day.

1/ Anti-Stretch Mark Composition in Soft Capsule Form

| | |
|---|---|
| Extract of aerial parts of maca | 30 mg |
| Awara oil | 60 mg |
| Rapeseed oil rich in unsaponifiable | 300 mg |
| B vitamin (B1, B2, B3, B5, B6, B9, B12) | q.s. 100% RDA |
| Tocotrienols | q.s. 50% RDA |
| Vitamin E | |
| Beeswax | |
| Soy lecithin | |
| Alimentary gelatin | |
| Glycerine q.s. 1 soft capsule | |

This composition is administered with 4 to 6 capsules of 500 mg per day.

2/ Anti-Hair Loss Tablets

| | |
|---|---|
| Extract of aerial parts of maca | 25 mg |
| Cereal extract (wheat, buckwheat, millet, spelt) rich in thioamino acids | 200 mg |
| Vitamin C | q.s. 50% RDA |
| Glycosaminoglycans from fish cartilage | 200 mg |
| Glucidex IT 19 (compression agent) | q.s. |
| | 1 × 800 mg tablet. |

This composition is administered with 5 to 8 tablets per day.

3/ Slimming Powder Stick Example

| | |
|---|---|
| Extract of aerial parts of maca | 100 mg |
| Tea extract rich in polyphenols | 100 mg |
| Grape extract rich in OPC | 50 mg |
| Betaglucans of plant origin | 100 mg |
| Xanthan gum | 1 mg |
| Sodium ascorbate | 0.3 mg |
| Maltodextrin | q.s. 5 g. |

This composition is administered twice daily.

Example 6: Biological Activities

1. Strengthening of Vessel Walls
a. Activity on Endothelial Cells

The effect of Maca leaf extract on dermal endothelial cells was studied by means of PCR array screening.

Endothelial cells are the constituent cells of the vessel wall and thus have a major role in maintaining vascular equilibrium and regulate interactions between the blood vessel and the surrounding tissue (dermis).

Materials and Methods:

Human microvascular endothelial cells were treated with 0.005% and 0.01% (w/v of active substance) Maca leaf extract (MC) for 24 hours.

After incubation, the gene expression of various markers was analysed by means of real-time quantitative RT-PCR using a PCR array.

Results and Conclusion:

The screening results on endothelial cells demonstrated that Maca leaf extract (table 1):

stimulates the gene expression of molecules involved in strengthening vessels: angiopoietin 1 (role in vessel establishment and stabilisation), serpin 1 (anti-protease), cadherin 5, fibrillin 1, integrin αV (cell/cell or cell/matrix adhesion molecules involved in vessel stabilisation), α SMA or α smooth muscle actin and troponin 1 (strengthening vessels/elasticity);

stimulates the gene expression of molecules involved in vessel tonicity: calmodulin (vessel permeability control), endothelin 1 and ECE1 or Endothelin Converting Enzyme 1 (vasoconstriction);

stimulates the gene expression of defence molecules: Haem Oxygenase 1 (protective role by preventing free haem from taking part in pro-oxidant reactions) and thioredoxin (repair of oxidative damage to proteins); and inhibits the gene expression of molecules involved in inflammation: CSF1 or macrophage colony-stimulating factor 1 (macrophage production/differentiation/function control) and E-selectin (adhesion molecule, role in inflammatory cell recruitment).

These effects indicate a vessel tonicity stimulating and blood vessel strengthening activity.

TABLE 1

PCR array activity screening on endothelial cells

| | Gene expression (Relative quantity in % with respect to control cells) | | |
|---|---|---|---|
| | Control cells | 0.005% MC | 0.01% MC |
| Vessel strengthening | | | |
| Angiopoietin 1 | 100 | 142 | 207 |
| Serpin 1 | 100 | 139 | 157 |
| Cadherin 5 | 100 | 121 | 198 |
| Fibrillin 1 | 100 | 155 | 199 |
| Integrin αV | 100 | 145 | 174 |
| α SMA | 100 | 119 | 147 |
| Troponin 1 | 100 | 116 | 201 |
| Vessel tonicity | | | |
| Calmodulin | 100 | 121 | 151 |
| Endothelin 1 | 100 | 119 | 144 |
| ECE 1 | 100 | 117 | 162 |
| Response to stress | | | |
| Haem oxygenase 1 | 100 | 143 | 158 |
| Thioredoxin | 100 | 131 | 140 |
| Inflammation | | | |
| CSF 1 | 100 | 57 | 106 |
| E-Selectin | 100 | 49 | 69 |

2. Protection and Strengthening of the Dermal Matrix
a. Activity on Dermal Matrix Markers The activity of Maca leaf extract on the dermal matrix was tested in dermal fibroblasts by analysing the gene expression of various markers:

type I collagen, the main constituent of the dermal extracellular matrix, responsible for skin firmness and resistance;

elastin, responsible for elasticity of the skin;

MMP1 (matrix metalloprotease-1), responsible for type I and III collagen degradation;

dermatopontin which is involved in assembling collagen fibres and is important for maintaining the dermal extracellular matrix structure and tissue flexibility;

decorin which binds with collagen fibres to prevent MMP1 cleavage;

fibronectin: high-molecular weight glycoprotein involved in the dermal extracellular matrix structure;

hyaluronan synthase 2: enzyme involved in forming hyaluronic acid, an important hygroscopic molecule for skin moisturisation and density.

Materials and Methods:

Normal human dermal fibroblasts were treated for 24 hours with 0.002% and 0.005% (w/v of active substance) Maca leaf extract (MC) or with 5 ng/ml TGFβ1 (reference).

At the end of incubation, the gene expression of various dermal matrix markers was analysed by means of real-time RT-PCR.

The results were analysed statistically by means of a one-factor ANOVA followed by a Dunnett test.

Results and Conclusion:

As shown in table 2, Maca leaf extract significantly increased the gene expression of collagen I, elastin, dermatopontin, decorin, fibronectin and hyaluronan synthase 2.

Moreover, Maca leaf extract significantly inhibited the gene expression of MMP1.

These results indicate a strengthening of the dermal extracellular matrix.

TABLE 2

Gene expression of dermal matrix markers in fibroblasts (Relative Quantity)

|  | Control | TGFβ1 |  | 0.002% MC |  | 0.005% MC |  |
| --- | --- | --- | --- | --- | --- | --- | --- |
| Collagen I | 1.00 | 1.40 | +40% | 1.59 | +59% ($p < 0.001$) | 1.23 | +23% |
| Elastin | 1.00 | 1.57 | +57% | 1.66 | +66% ($p < 0.05$) | 1.25 | +25% |
| MMP1 | 1.00 | 0.22 | −78% ($p < 0.001$) | 0.58 | −42% ($p < 0.001$) | 0.72 | −28% ($p < 0.05$) |
| Dermatopontin | 1.00 | 1.34 | +34% ($p < 0.05$) | 1.37 | +37% ($p < 0.01$) | 1.28 | +28% ($p < 0.05$) |
| Decorin | 1.00 | nd | nd | 1.35 | +35% ($p < 0.05$) | 1.15 | +15% |
| Fibronectin | 1.00 | 2.41 | +141% ($p < 0.001$) | 1.53 | +53% ($p < 0.01$) | 1.42 | +42% ($p < 0.05$) |
| Hyaluronan synthase 2 | 1.00 | nd | nd | 1.40 | +40% ($p < 0.01$) | 1.20 | +20% | nd: not determined b. Activity on a Dermal Matrix Marker in Aged Fibroblasts

The effect of Maca leaf extract was tested in dermal fibroblasts prematurely aged by means of $H_2O_2$ treatment, by analysing the gene expression of biglycan.

Biglycan is a small proteoglycan influencing collagen fibrillogenesis.

Materials and Methods:

Normal human dermal fibroblasts were prematurely aged with 600 µM $H_2O_2$.

Fibroblasts were then incubated for 72 hours in the presence of 0.005% and 0.01% (w/v of active substance) Maca leaf extract (MC) or 10 ng/ml TGFβ extract (reference).

After incubation, the gene expression of biglycan was analysed by means of real-time quantitative RT-PCR.

Results and Conclusion:

Inducing fibroblast ageing with $H_2O_2$ treatment inhibited the expression of biglycan; Maca leaf extract made it possible to restore this expression (table 3).

Maca leaf extract protects the dermal matrix under ageing conditions.

TABLE 3

Gene expression of biglycan in dermal fibroblasts aged with $H_2O_2$
Bigylcan (Relative quantity)

| Control fibroblasts | Aged fibroblasts ($H_2O_2$) | 0.005% MC | 0.01% MC |
| --- | --- | --- | --- |
| 123 | 100 | 112 | 142 | c. Elastase Production Inhibition

Under the influence of various stimuli (inflammation, UV radiation, etc.), human neutrophils release oxygenated species and enzymes such as elastase.

An excess of elastase may degrade skin matrix proteins, such as elastin, proteoglycans, collagen, decorin, etc.

The effect of Maca leaf extract was evaluated on the release of elastase by human neutrophils.

Materials and Methods:

Human neutrophils were treated for 15 minutes with 0.005 and 0.01% (w/v of active substance) Maca leaf extract (MC) or with 10 µg/ml Boswellic acid (reference) and stimulated with 1 µM calcium ionophore A23187, for 10 minutes.

The release of elastase was evaluated by measuring the elastase activity with a spectrophotometric method.

The results were analysed statistically using a Student's t test.

Results and Conclusion:

Maca leaf extract significantly inhibited the release of elastase by neutrophils (table 4).

These results demonstrate a protective effect with respect to the dermal matrix.

TABLE 4

Release of elastase by neutrophils

|  | Elastase (net release; %) | Inhibition |  |
| --- | --- | --- | --- |
| Calcium ionophore | 100 ± 1.70 |  |  |
| 10 µg/ml Boswellic acid | 50.90 ± 7.49 | −49% | $p < 0.001$ |
| 0.005% MC | 81.40 ± 0.90 | −19% | $p < 0.001$ |
| 0.01% MC | 60.24 ± 596 | −40% | $p < 0.001$ |

3. Anti-Inflammatory and Anti-Oxidant Defences
a. Protection Against Lipid Peroxidation
Materials and Methods:

Jurkat cell lines were pre-incubated for 45 minutes in the presence of 0.005% and 0.01% (w/v of active substance) Maca leaf extract (MC) or 100 µM BHT (reference) and in the presence of the C11-Fluor fluorescent probe, specific for lipid peroxidation.

The cells were then irradiated with UVA+B and incubated for 30 minutes in the presence of MC or BHT.

At the end of incubation, the quantity of lipid peroxides was evaluated by means of a flow cytometry analysis of the fluorescence intensity (inversely proportional to oxidation).

The results were analysed were analysed statistically using a Student's t test.
Results and Conclusion:

Maca leaf extract significantly protected the cells against lipid peroxidation induced by UV radiation (table 5).

TABLE 5

UV-induced lipid peroxidation

| | Lipid peroxidases (% irradiated reference) | Protection (%) | |
|---|---|---|---|
| Irradiated cells (UV) | 100 | | |
| 100 µM BHT | 64 | 49% | p < 0.01 |
| 0.005% MC | 62 | 52% | p < 0.01 |
| 0.01% MC | 59 | 56% | p < 0.01 | b. Inhibition of PMA-Induced Inflammation
Materials and Methods:

Human keratinocytes (NCTC-2544 line) were pre-incubated or not (control) with 0.005% and 0.01% (w/v of active substance) maca leaf extract (MC) or reference anti-inflammatory molecules ($10^{-7}$M dexamethasone; $10^{-6}$M indometacin) for 24 hours. The cells were then treated with 0.1 µg/ml PMA (Phorbol Myristate Acetate) for 24 hours, also in the presence of MC or the references.

Following the treatment, the quantities of IL8 (interleukin8) and PGE2 (prostaglandin E2) secreted were measured by means of ELISA in the culture supernatants.

The results were analysed statistically using a Student's t test.
Results and Conclusion:

Maca leaf extract strongly and significantly inhibited production of the inflammatory mediators IL8 and PGE2 stimulated by PMA in keratinocytes (table 6).

These results demonstrate the anti-inflammatory activity of Maca leaf extract.

TABLE 6

IL8 and PGE2 production by keratinocytes

| | IL8 (ng/ml %) | Inhibition | |
|---|---|---|---|
| Control cells | 0.1 ± 0.0 | | |
| 0.1 µg/ml PMA | 50.1 ± 1.8 | | |
| $10^{-7}$M dexamethasone | 7.4 ± 0.08 | 85% | p < 0.001 |
| 0.005% MC | 24.7 ± 0.8 | 51% | p < 0.001 |
| 0.01% MC | 19.3 ± 0.8 | 62% | p < 0.001 |

| | PGE2 (ng/ml %) | Inhibition | |
|---|---|---|---|
| Control cells | 0.039 ± 0.0 | | |
| 0.1 µg/ml PMA | 138.4 ± 10.6 | | |
| $10^{-6}$M indometacin | 0.039 ± 0.0 | 100% | p < 0.001 |

TABLE 6-continued

IL8 and PGE2 production by keratinocytes

| 0.005% MC | 21.8 ± 1.8 | 84% | p < 0.001 |
|---|---|---|---|
| 0.01% MC | 9.8 ± 0.0 | 93% | p < 0.001 | c. Inhibition of *P. acnes*-Induced Inflammation

The protective effect of Maca leaf extract in respect of inflammation induced by *Propionibacterium acnes* was studied on keratinocytes colonised by this bacteria.
Materials and Methods:

Human keratinocytes (HaCaT line) were pre-incubated for 48 hours in the presence of 0.008% and 0.031% (w/v of active substance) Maca leaf extract (MC) or reference inhibitor: nicotinamide.

The keratinocytes were then stimulated by incubating for 18 hours with a bacterial suspension of *P. acnes* (ATCC6919 strain).

At the end of incubation, the quantity of IL8 produced by the keratinocytes was measured in the culture supernatants using an ELISA technique.

The results were analysed statistically using a Student's t test: ns p>0.05 (non-significant); *p<0.05; p<0.01; *p<0.001.
Results and Conclusion:

FIG. 1 represents the production of IL8, in µg/ml, by keratinocytes stimulated with *P. acnes*, with a pre-incubation time of 18 hours, as a function of the active substance concentration in %.

Maca leaf extract significantly inhibited *P. acnes*-induced IL8 production on keratinocytes (FIG. 1).

Maca leaf extract thus modulates *P. acnes*-induced inflammation.

4. Lipogenesis Inhibition in Adipocytes
Materials and Methods:

Normal human adipocytes were incubated for 1 hour in the presence of 0.005% and 0.01% (w/v of active substance) Maca leaf extract or reference (20 µM cerulenin). After incubation, the radioactive marker [$^{14}$C]-acetate was added and the samples were incubated overnight.

At the end of incubation, the lipids were extracted and the incorporated radioactivity (corresponding to lipogenesis) was measured by means of liquid scintillation.

The results were analysed statistically using a Student's t test.
Results and Conclusion:

Maca leaf extract significantly inhibited lipid neosynthesis by adipocytes (table 7).

In this way, this extract thus has a slimming effect.

TABLE 7

Evaluation of lipogenesis in adipocytes

| | Acetate incorporation (cpm) | Inhibition | |
|---|---|---|---|
| Control cells | 32895 ± 1358 | | |
| Reference (Cerulenin) | 14934 ± 671 | 55% | p < 0.001 |
| 0.005% MC | 27331 ± 700 | 17% | p < 0.05 |
| 0.01% MC | 23664 ± 960 | 28% | p < 0.01 |

The invention claimed is:

1. A method for treating obesity, treating cellulite, reducing wrinkles, increasing skin elasticity, and/or slimming, comprising administering to a subject in need thereof an effective amount of a composition comprising an extract of Maca leaves or leafy stems,
   wherein said extract comprises at least 5% polyphenols by weight, expressed in gallic acid equivalents, with respect to the dry weight of the extract,
   wherein said polyphenols have a flavonoid content greater than 2% expressed in rutin equivalents, with respect to the total dry weight of the extract.

2. The method according to claim 1, wherein said composition contains 0.001 to 10% by weight of said extract, expressed as a percentage of dry extract.

3. The method according to claim 1, wherein said flavonoids contain quercetin, kaempferol, derivatives thereof or mixtures thereof.

4. The method according to claim 3, wherein said flavonoids contain quercetin, kaempferol, derivatives thereof or mixtures thereof at a concentration of at least 30% by weight, expressed in gallic acid equivalents, with respect to the total weight of the flavonoids.

5. The method according to claim 4, wherein said flavonoids contain quercetin, kaempferol, derivatives thereof or mixtures thereof at a concentration of at least 50% by weight, expressed in gallic acid equivalents, with respect to the total weight of the flavonoids.

6. The method according to claim 1, wherein said composition further comprises a suitable excipient.

7. The method according to claim 1, wherein said extract is an extract of Maca leaves.

8. The method according to claim 1, wherein said extract is a glycol/water or glycerol/water extract.

9. The method according to claim 1, wherein said composition further comprises a compound selected from the group consisting of emollients, moisturizing agents, keratoregulators, keratolytics, skin barrier healing and/or remodeling agents, PPAR, RXR or LXR agonists, sebo-regulating agents, anti-irritant and/or anti-inflammatory and/or soothing agents, anti-oxidant agents, anti-ageing agents, depigmenting or hypopigmenting agents, pigmenting agents, lipolytic agents or lipogenesis inhibitors or anti-cellulite or slimming agents, mineral or organic sun filters and screens, antifungal compounds, preservatives, antibacterial agents, pre and probiotics, antibiotics and immunomodulators.

10. The method according to claim 1, wherein said composition further comprises a compound selected from:
   skin barrier healing and/or remodelling agents, optionally panthenol, arabinogalactan and zinc oxide,
   sebo-regulating agents, optionally chosen from the group consisting of 5-alpha reductase inhibitors, zinc derivatives, spironolactone, and linoleic acid,
   anti-inflammatory and/or anti-irritant and/or soothing agents, optionally arabinogalactan,
   hypopigmenting or depigmenting agents, optionally N-undecylenoyl-L-phenylalanine,
   mineral and/or organic sun screens or filters, optionally UVB and/or UVA sun filters or screens, and
   preservatives optionally chosen from capryloyl glycine, glyceryl caprylate, hexanediol, sodium levulinate, zinc and copper derivatives.

11. The method according to claim 1, wherein said composition is formulated for topical or oral administration.

12. The method according to claim 1 for treating obesity.

13. The method according to claim 1 for treating cellulite and/or for slimming.

14. The method according to claim 1 for reducing wrinkles and/or increasing skin elasticity.

* * * * *